US008962678B2

(12) United States Patent
Ota et al.

(10) Patent No.: US 8,962,678 B2
(45) Date of Patent: Feb. 24, 2015

(54) SENESCENCE INHIBITOR

(75) Inventors: Noriyasu Ota, Haga-gun (JP); Satoshi Haramizu, Haga-gun (JP); Takatoshi Murase, Haga-gun (JP)

(73) Assignee: Kao Corporation, Tokyo (JP)

( * ) Notice: Subject to any disclaimer, the term of this patent is extended or adjusted under 35 U.S.C. 154(b) by 382 days.

(21) Appl. No.: 12/307,330

(22) PCT Filed: Jun. 29, 2007

(86) PCT No.: PCT/JP2007/000716
§ 371 (c)(1),
(2), (4) Date: Jan. 2, 2009

(87) PCT Pub. No.: WO2008/004340
PCT Pub. Date: Jan. 10, 2008

(65) Prior Publication Data
US 2009/0281174 A1    Nov. 12, 2009

(30) Foreign Application Priority Data

| Jul. 5, 2006 | (JP) | ................................ 2006-185466 |
| Aug. 10, 2006 | (JP) | ................................ 2006-217960 |
| Aug. 10, 2006 | (JP) | ................................ 2006-218140 |
| Mar. 13, 2007 | (JP) | ................................ 2007-063521 |

(51) Int. Cl.
*A01N 43/16*    (2006.01)
*A61K 31/35*    (2006.01)
*A61K 39/00*    (2006.01)

(52) U.S. Cl.
USPC ........................................ 514/456; 424/185.1

(58) Field of Classification Search
USPC ......................................................... 514/456
See application file for complete search history.

(56) References Cited

U.S. PATENT DOCUMENTS

| 5,788,971 A | 8/1998 | Togasaki |
| 2004/0047896 A1 | 3/2004 | Malnoe et al. |
| 2004/0087516 A1 | 5/2004 | Rosenbloom |
| 2004/0120983 A1* | 6/2004 | Connolly ...................... 424/439 |
| 2004/0126461 A1 | 7/2004 | Lines et al. |
| 2005/0175565 A1 | 8/2005 | Duranton et al. |
| 2006/0052455 A1 | 3/2006 | Koga et al. |
| 2007/0004650 A1 | 1/2007 | Shimotoyodome et al. |
| 2007/0149466 A1 | 6/2007 | Milburn et al. |
| 2007/0149619 A1 | 6/2007 | Takagi et al. |
| 2009/0148554 A1 | 6/2009 | Kataoka et al. |

FOREIGN PATENT DOCUMENTS

| JP | 60-156614 | 8/1985 |
| JP | 4-352726 | 7/1992 |
| JP | 4-253918 | 9/1992 |
| JP | 8-169831 A | 7/1996 |
| JP | 9-59154 A | 3/1997 |
| JP | 09322716 A * | 12/1997 |
| JP | 10-17585 | 1/1998 |
| JP | 10 175858 | 6/1998 |
| JP | 11-43432 | 2/1999 |
| JP | 2000-26289 | 1/2000 |
| JP | 2000-26290 | 1/2000 |
| JP | 2001-89387 | 4/2001 |
| JP | 2002-338464 | 11/2002 |
| JP | 2003-12539 | 1/2003 |
| JP | 2003-261456 | 9/2003 |
| JP | 2003 286167 | 10/2003 |
| JP | 2004-51580 | 2/2004 |
| JP | 2004-59518 | 2/2004 |
| JP | 2004-115438 | 4/2004 |
| JP | 2004-182705 | 7/2004 |
| JP | 2004 519241 | 7/2004 |
| JP | 2004 331724 | 11/2004 |
| JP | 2005-89384 | 4/2005 |
| JP | 2005-97273 | 4/2005 |
| JP | 2005-281285 | 10/2005 |
| JP | 2005-535617 A | 11/2005 |
| JP | 2006-16409 | 1/2006 |
| JP | 2006-28194 | 2/2006 |
| JP | 2006-62976 | 3/2006 |
| JP | 2006-63038 | 3/2006 |
| JP | 2006-122004 | 5/2006 |
| JP | 2006-158379 A | 6/2006 |
| KR | 10-2005-0034568 A | 4/2005 |
| WO | 01 21186 | 3/2001 |
| WO | WO 01/21186 A1 | 3/2001 |
| WO | WO 0212882 A2 * | 2/2002 |
| WO | 2004 037015 | 5/2004 |
| WO | WO 2005/104873 A1 | 11/2005 |
| WO | WO 2005/123058 A1 | 12/2005 |
| WO | 2006 051980 | 5/2006 |
| WO | WO 2007/006135 A1 | 1/2007 |

(Continued)

OTHER PUBLICATIONS

Dulloo, Am J Clin Nutr 1999;70:1040-5. Efficacy of a green tea extract rich in catechin polyphenols and caffeine in increasing 24-h energy expenditure and fat oxidation in humans.*

(Continued)

*Primary Examiner* — Layla Soroush
(74) *Attorney, Agent, or Firm* — Oblon, Spivak, McClelland, Maier & Neustadt, L.L.P.

(57) ABSTRACT

Provision of a drug, a quasi-drug, and a food or beverage, which are effective for senescence inhibition, mitochondrial function improvement, muscle dysfunction inhibition, muscular atrophy inhibition, prevention of a bedridden state, muscle senescence inhibition, or motor function improvement. A senescence inhibitor, a mitochondrial function-improving agent, a muscle dysfunction inhibitor, a muscular atrophy inhibitor, and an agent for preventing a bedridden state, containing a catechin as an effective ingredient. A muscle senescence inhibitor and a motor function-improving agent, containing a catechin and an amino acid as effective ingredients.

5 Claims, 2 Drawing Sheets

(56) References Cited

FOREIGN PATENT DOCUMENTS

| WO | 2007 020917 | 2/2007 |
|---|---|---|
| WO | WO 2007/042271 A2 | 4/2007 |
| WO | WO 2007/042271 A3 | 4/2007 |
| WO | WO 2007/056307 A2 | 5/2007 |
| WO | WO 2007/056307 A3 | 5/2007 |

OTHER PUBLICATIONS

Fiatarone et al. The etiology and reversibility of muscle dysfunction in the aged. Journal of Gerontology; Sep. 1993; 48).*

Liou et al. ("Physical disability and obesity." Nutrition reviews 63.10 (2005): 321-331).*

Nagasawa, T et al., "Effects of leucine administration on protein degradation and oxidative stress in disuse muscle", Reports of the Research Committee of Essential Amino Acids, No. 175, pp. 59-64, 2006, (with partial English translation).

Iwanami Lectures, Gendai Igaku no Kiso ("Basic Modern Medicine"), vol. 12, No. 2, 1999, pp. 55-58 with partial translation.

Oliver M. Dorchies, et al., "Green tea extract and its major polyphenol (−)-epigallocatechin gallate improve muscle function in a mouse model for Duchenne muscular dystrophy", American Journal of Physiology—Cell Physiology, vol. 290, No. 2, 2006, pp. C616-C625.

Annemarie E. Brouwer, et al., "Effects of Leucine on Insulin Secretion and Beta Cell Membrane Potential in Mouse Islets of Langerhans", Pancreas, vol. 6, No. 2, 1991, pp. 221-228.

Stephen J. Crozier, et al., "Oral Leucine Administration Stimulates Protein Synthesis in Rat Skeletal Muscle", The Journal of Nutrition, vol. 135, No. 3, 2005, pp. 376-382.

M. V. Ramana Kumari, et al., "Effect of "βCatechin" on the Life Span of Senescence Accelerated Mice (SAM-P8 Strain)" Biochemistry and Molecular Biology International, vol. 41, No. 5, XP008111412, Apr. 1997, pp. 1005-1011.

M. Komatsu, et al., "The Efficacy of an Antioxidant Cocktail on Lipid Peroxide Level and Superoxide Dismutase Activity in Aged Rat Brain and DNA Damage in Iron-Induced Epileptogenic Foci", Toxicology, vol. 148, No. 2-3, XP008111397, Aug. 7, 2000, pp. 143-148.

Timo M. Buetler, et al., "Green Tea Extract Decreases Muscle Necrosis in *mdx* Mice and Protects Against Reactive Oxygen Species", The American Journal of Clinical Nutrition, vol. 75, No. 4, XP002459513, Apr. 2002, pp. 749-753.

Koichi Iwai, et al., "Effect of Tea Catechins on Mitochondrial DNA 4977-bp Deletions in Human Leucocytes", Mutation Research, vol. 595, No. 1-2, XP025250669, Mar. 20, 2006, pp. 191-195.

Takatoshi Murase, et al., "Green Tea Extract Improves Running Endurance in Mice by Stimulating Lipid Utilization During Exercise", American Journal of Physiology. Regulatory, Integrative and Comparative Physiology, vol. 290, No. 6, XP008080359, Jan. 12, 2006, pp. R1550-R1556.

Anjali Singal, et al., "Green Tea Extract and Catechin Ameliorate Chronic Fatigue-Induced Oxidative Stress in Mice", Journal of Medicinal Food, vol. 8, No. 1, XP003015493, Jan. 1, 2005, pp. 47-52.

Mohd Najmul Ghani Khan, "Hab-e-Chai Deegar Qawi Tar", Key Attributes of TKDL NA4/3925, XP003025360, 1928, pp. 1-4 (with English translation).

Mohd Najmul Ghani Khan, "Habb-e-chai", Key Attributes of TKDL NA4/3924, XP003025359, 1928, pp. 1-3 (with English translation).

Mohd Akmal Khan, "Qahwah Bara-e-Faalij Wa Laqwa", Key Attributes of TKDL AH5/2667, XP003025358, 2000, pp. 1-3 (with English translation).

Mohd Akmal Ghani Khan, "Qahwah Deegar Bara-e-Faalij Wa Laqwa", Key Attributes of TKDL AH5/2668, XP003025357, 2000, pp. 1-3.

Office Action issued Aug. 9, 2011 in Japan Application No. 2006-185466 (With English Translation).

T. Nagasawa, et al., "Suppression of Oxidative Modification of Skeletal Muscle Protein by Dietary Catechin", Hissu Amino-san Kenkyu (Essential Amino Acid Study), 1999, No. 155, pp. 74-79 (With Computer-Generated English Translation).

Office Action issued Dec. 25, 2012 in Japanese Patent Application No. 2007-186743 with English language translation.

Mayumi Sato, et al. "leucine toyo ni yoru haiiseikinisyuku kaizen hoho (Effect of Improving disuse muscle atrophy by leucine administration)" Summary of Annual Meeting of Japan Society for Bioscience, Biotechnology and Agrochemistry, 2C24p24, Mar. 5, 2006, vol. 2006, p. 136 (with unedited computer-generated English translation).

Office Action issued on Jan. 21, 2013, in Chinese Patent Application No. 200780025498.5 with English translation.

Japanese Office Action issued Oct. 2, 2012 in Patent Application No. 2007-186743 with English Translation.

Joshua C. Anthony, et al., "Orally Administered Leucine Stimulates Protein Synthesis in Skeletal Muscle of Postabsorptive Rats in Association with Increased eIF4F Formation", Biochemical and Molecular Action of Nutrients, vol. 130, (2000), pp. 139-145.

* cited by examiner

SENESCENCE INHIBITOR

TECHNICAL FIELD

The present invention relates to a senescence inhibitor, a mitochondrial function-improving agent, a muscle dysfunction inhibitor, a muscular atrophy inhibitor, an agent for preventing a bedridden state, a muscle senescence inhibitor, and a motor function-improving agent.

BACKGROUND ART

Senescence is generally categorized into physiological senescence and pathological senescence. Physiological senescence inevitably occurs through aging and involves changes in hair, skin, eyes, bones, brain, etc. and reduction of motor function and energy metabolism. Recent years' studies have suggested that reduction of energy metabolism due to senescence is related to mitochondrial dysfunction such as mutation or damage of mitochondrial DNA (Non-Patent Document 1).

When muscle force and physical endurance are reduced through senescence, daily life activity is impaired. Also, reduction of energy metabolism and mitochondrial function causes unbalanced energy intake and consumption, possibly causing life-style-related diseases such as obesity and diabetes. In advanced countries, prevention of life-style-related diseases is an important target from the viewpoint of improvement of quality-of-life (QOL). Therefore, in order to improve QOL and prolong a healthy period of life, important factors are to prevent aging-related reduction of physiological function; i.e., senescence, and particularly to maintain physical endurance, suppress fatigue, maintain energy metabolism at a high level, and improve mitochondrial function.

Generally, muscular atrophy, which involves reduction in muscle mass and muscle force, includes disuse muscular atrophy, sarcopenia, etc. When muscular atrophy occurs, muscle function is reduced. Particularly in the case of an aged person, muscular atrophy and reduced muscle force due to senescence were observed, and muscle damage and fracture tend to occur. During a period of treatment and curing thereof under restriction of movement through rest or by means of a cast, disuse muscular atrophy and muscle dysfunction are accelerated. Aged people are readily involved in such a malcycle, and in the worst case bedridden. Therefore, in order to improve daily life functions, prolong a healthy period of life, and maintain quality-of-life (QOL), disuse muscular atrophy and muscle dysfunction are to be prevented through physical exercise of certain strength, to thereby maintain motor function and total body functions in a favorable state.

Senescence progresses by genetic and environmental factors and is considered to be retarded through improvement of environmental factors including those related to life style (e.g., diet or physical exercise). For preventing a decrease in motor performance or muscle function and muscular atrophy which accompany senescence, a repeated physical exercise with an appropriate strength during a healthy period, a physical rehabilitation therapy, etc. are effective means. Particularly in the case of an aged person, repeated physical exercise with an appropriate strength, physical rehabilitation therapy, etc. are effective. However, since such exercises may involve possible injuries or encounter difficulty in maintenance of motivation, there is demand for safer and more effective prevention means.

Some components which can suppress physical senescence have already been known. For example, there have been disclosed an anti-aging composition containing a bio-collagen synthesis promoter and an abnormal protein remover as an skin senescence inhibition component (Patent Document 1), an anti-aging agent containing a carrot leaf extract as an effective ingredient (Patent Document 2), and an anti-aging composition containing a Japanese horseradish (wasabi) extract and a rush extract as an essential ingredient (Patent Document 3).

Also disclosed are the following: a cell senescence inhibitor containing a Mannen-take solvent extract as a telomere shortening suppression component (Patent Document 4), and cacao and/or cacao mass (Patent Document 5), an organic germanium compound (Patent Document 6) and L-arginine, phosphatidylserine, docosahexanoic acid, ginkgo leaves or ginkgo leaf extract, and tocopherol (Patent Document 7), as a brain senescence inhibitor. Also disclosed is an L-arginine-containing preventive/therapeutic composition for the onset of clinical symptoms in a disease caused by mitochondrial function abnormality (Patent Document 8).

In addition to physical exercises and physical therapy, screening of components for preventing muscular atrophy, muscle dysfunction associated with muscular atrophy, and a bedridden state has been carried out through nutritional approaches. For example, the following are disclosed: senescence inhibition by cystine and theanine (Patent Document 9), muscular atrophy inhibition by fruit-derived polyphenol (Patent Document 10), muscular protein degradation inhibition by lycopene (Patent Document 11), inhibition of decrease in motor performance by an organic acid having 2 or more carboxyl groups or a salt thereof as an active ingredient (Patent Document 12), astaxanthin and/or an ester thereof as a fatigue-preventing agent (Patent Document 13), proanthocyanidine serving as a muscular atrophy inhibitor and motor function improving agent (Patent Documents 14 and 15), and relaxation of oxidative stress of muscle by superoxide dismutase (Patent Document 16). However, at present, studies have not yet been conducted on the actual effects on reduction of muscle force and muscular atrophy accompanying aging.

Meanwhile, physiologically useful properties of catechins contained in green tea, black tea, cacao beans, etc. have already been reported. For example, cholesterol level increase suppression action (Patent Document 17), blood sugar level increase suppression action (Patent Document 18), arteriosclerosis prevention action (Patent Document 19), physical endurance improving action (Patent Document 20), and muscular dystrophy suppression action (Non-Patent Document 2) are reported.

However, hitherto, any inhibitory actions of catechin on senescence and mitochondrial function, particularly decrease in physical endurance and energy metabolism, fatigue, and dysfunction of mitochondria, have not been known.

Actions of catechin on disuse muscular atrophy and muscle dysfunction associated therewith have also not been reported.

Meanwhile, leucine, valine, and isoleucine, which are branched-chain amino acids, are known as useful agents: an impaired glucose tolerance treatment agent (Patent Document 21), an agent for maintaining instantaneous power and endurance of muscle (Patent Document 22), and a muscle pain and stiffness reliever (Patent Document 23). Among them, leucine is reported to have an insulin secretion promoting action (Non-Patent Document 3), a muscular protein synthesis action (Non-Patent Document 4), etc. However, the actions of catechins, amino acids, and a combination thereof on an inhibitory action on decrease in muscle weight and muscle force accompanying senescence have not been known.

Patent Document 1: JP-A-2004-115438
Patent Document 2: JP-A-2004-51580

Patent Document 3: JP-A-2006-63038
Patent Document 4: JP-A-2003-12539
Patent Document 5: JP-A-2005-281285
Patent Document 6: JP-A-H11-43432
Patent Document 7: JP-A-2003-261456
Patent Document 8: JP-A-2004-182705
Patent Document 9: WO 2005-123058, pamphlet
Patent Document 10: JP-A-2001-89387
Patent Document 11: JP-A-2004-59518
Patent Document 12: JP-A-H10-17585
Patent Document 13: JP-A-2006-16409
Patent Document 14: JP-A-2002-338464
Patent Document 15: JP-A-2005-97273
Patent Document 16: JP-A-2006-62976
Patent Document 17: JP-A-S60-156614
Patent Document 18: JP-A-H4-253918
Patent Document 19: JP-A-H4-352726
Patent Document 20: JP-A-2005-89384
Patent Document 21: JP-A-2006-28194
Patent Document 22: JP-A-2000-26290
Patent Document 23: JP-A-2000-26289
Non-Patent Document 1: Iwanami Lectures, *Gendai Igaku no Kiso* ("Basic Modern Medicine"), vol. 12, No. 2, pp. 55-58, 1999
Non-Patent Document 2: Dorchies O. M. et al, AJP-Cell Physiol., vol. 290, No. 2, pp. 616-25, 2006
Non-Patent Document 3: Brouwer A. E. et al, Pancreas, vol. 6, No. 2, pp. 221-8, 1991
Non-Patent Document 4: Crozier S. J. et al, J. Nutr., vol. 135, No. 3, pp. 376-82, 2005

DISCLOSURE OF THE INVENTION

Accordingly, the present invention is directed to the following.
(1) A senescence inhibitor, containing a catechin as an effective ingredient.
(2) A mitochondrial function-improving agent, containing a catechin as an effective ingredient.
(3) A food or beverage for senescence inhibition, containing a catechin.
(4) A muscle dysfunction inhibitor, containing a catechin as an effective ingredient.
(5) A muscular atrophy inhibitor, containing a catechin as an effective ingredient.
(6) An agent for preventing a bedridden state, containing a catechin as an effective ingredient.
(7) A food or beverage for inhibiting muscle dysfunction, for inhibiting muscular atrophy or for preventing a bedridden state, containing a catechin.
(8) A muscle senescence inhibitor, containing (a) a catechin and (b) an amino acid selected from a branched-chain amino acid and taurine as effective ingredients.
(9) A motor function-improving agent, containing (a) a catechin and (b) an amino acid selected from a branched-chain amino acid and taurine as effective ingredients.
(10) An agent for preventing a bedridden state, containing (a) a catechin and (b) an amino acid selected from a branched-chain amino acid and taurine as effective ingredients.
(11) A food or beverage for inhibiting muscle senescence, for improving a motor function or for preventing a bedridden state, containing (a) a catechin and (b) an amino acid selected from a branched-chain amino acid and taurine.
(12) Use of a catechin as a senescence inhibitor or a mitochondrial function-improving agent.
(13) Use of a catechin for producing a senescence inhibitor or a mitochondrial function-improving agent.
(14) Use of a catechin as a muscle dysfunction inhibitor, a muscular atrophy inhibitor or an agent for preventing a bedridden state.
(15) Use of a catechin for producing a muscle dysfunction inhibitor, a muscular atrophy inhibitor or an agent for preventing a bedridden state.
(16) Use of (a) a catechin and (b) an amino acid selected from a branched-chain amino acid and taurine, as a muscle senescence inhibitor, a motor function-improving agent, or an agent for preventing a bedridden state.
(17) Use of (a) a catechin and (b) an amino acid selected from a branched-chain amino acid and taurine, for producing a muscle senescence inhibitor, a motor function-improving agent, or an agent for preventing a bedridden state.
(18) A method for inhibiting senescence or for improving a mitochondrial function, wherein the method comprises administering an effective amount of a catechin to a subject in need thereof.
(19) A method for inhibiting muscle dysfunction, for inhibiting muscular atrophy or for preventing a bedridden state, wherein the method comprises administering an effective amount of a catechin to a subject in need thereof.
(20) A method for inhibiting muscle senescence, for improving a motor function or for preventing a bedridden state, wherein the method comprises administering effective amounts of (a) a catechin and (b) an amino acid selected from a branched-chain amino acid and taurine to a subject in need thereof.

DETAILED DESCRIPTION OF THE PRESENT INVENTION

Figure 1:
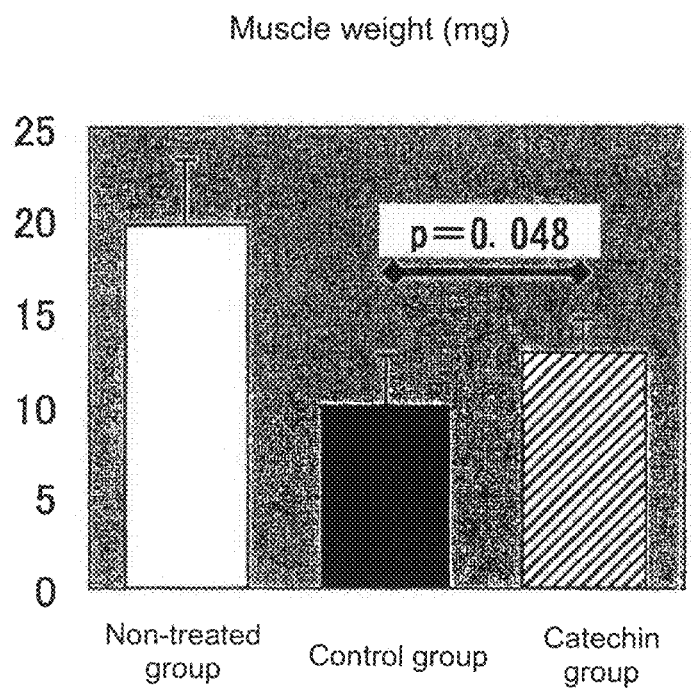
FIG. 1
A graph showing masses of soleus muscle (mg) of a control group and a catechin group treated with tenotomy, and a non-treated group.

The present invention is directed to provision of a drug, a quasi-drug and a food and beverage, which are effective for senescence inhibition, mitochondrial function improvement, muscle dysfunction inhibition, muscular atrophy inhibition, prevention of a bedridden state, muscle senescence inhibition and motor function improvement, and are well-known food ingredients and highly safe.

The present inventors have conducted extensive studies and have found that the following: (1) a catechin can inhibit dysfunctions accompanying senescence such as decrease in physical endurance, fatigue, decrease in energy metabolism, and dysfunction of mitochondria, and are useful as a food and beverage, a drug, etc. which are effective for senescence inhibition and mitochondrial function improvement; (2) a catechin can inhibit muscle mass reduction and decrease in maximum muscle force under movement-restricted conditions, and is useful as a food and beverage, a drug, etc. which are effective for muscular atrophy inhibition and muscle force inhibition; and (3) combined use of a catechin and an amino acid selected from a branched-chain amino acid and taurine can inhibit decrease in muscle force and muscular atrophy accompanying senescence, improve a motor function, and prevent a bedridden state, and are useful as a food and beverage, a drug, etc. which are effective for muscle senescence inhibition and motor function improvement.

The senescence inhibitor, mitochondrial function-improving agent, muscle dysfunction inhibitor, muscular atrophy inhibitor, and agent for preventing a bedridden state according to the present invention each contain a catechin, which has a long history as a foodstuff, exhibits less adverse side effects, and ensures high safety during long-term administration or intake, as an effective ingredient. Therefore, these agents are useful as foods and beverages, drugs, etc. exhibiting effects in terms of senescence inhibition, specifically inhibition of decrease in functions which accompany senescence such as decrease in physical endurance, fatigue, decrease in energy metabolism and dysfunction of mitochondria; improvement of a motor function of muscle; inhibition of muscle dysfunction; or prevention of a bedridden state.

The muscle senescence inhibitor, motor function-improving agent, and agent for preventing a bedridden state according to the present invention each contain (a) a catechin and (b) an amino acid selected from a branched-chain amino acid and taurine as effective ingredients. The catechin and the amino acid described above ensure high safety during long-term administration or intake, and thus are useful as foods and beverages, drugs, etc. exhibiting effects in terms of inhibition of decrease in muscle force and muscular atrophy which accompany senescence.

As used herein, the term "senescence inhibition" refers to inhibition of a physiological change accompanying senescence. The physiological change includes decrease in physical endurance, fatigue, decrease in energy metabolism, and dysfunction of mitochondria. More specifically, the physiological change includes decrease in physical endurance, fatigue, decrease in energy metabolism, and dysfunction of mitochondria observed in aged people such as people of middle age (i.e., in their 30's or older).

The term "muscle senescence" refers to weakening of muscle accompanying senescence; for example, muscle dysfunctions (muscle force, muscle physical endurance, and instantaneous muscle power) or muscular atrophy. The term "motor function improvement" refers to maintenance or improvement of motor function through inhibition of muscle dysfunctions.

The term "muscular atrophy" refers to reduction of muscle amount due to reduction or contraction of muscular cells. The muscular atrophy includes muscle atrophy caused by long-term bed rest, fixation by a cast for treating fracture etc., or exposure to microgravity (also called disuse muscular atrophy), and muscle atrophy accompanying aging (called sarcopenia). Thus, the term "inhibition of muscular atrophy" refers to inhibition of reduction of muscle amount caused by non-moving conditions or aging.

The term "muscle dysfunction" refers to such a condition that muscle force, muscle physical endurance, instantaneous muscle force, etc. are decreased through change in structure or quality of muscle. Thus, the term "inhibition of muscle dysfunction" refers to inhibition of decrease in muscle force, muscle physical endurance, instantaneous muscle force, etc.

The "bedridden" refers to a complex symptom of disuse muscular atrophy and sarcopenia observed in aged people such as people of middle age (i.e., in their 30's or older). One case of a bedridden state is that, when an aged person hardly moves during treatment of cerebral stroke, fracture, etc., the person further decreases in muscle function, thereby being laid up, and becomes bedridden.

The term "catechin" in the present invention collectively refers to (A) non-epi-catechins such as catechin, catechin gallate, gallocatechin, and gallocatechin gallate; and (B) epi-catechins such as epicatechin, epigallocatechin, epicatechin gallate, and epigallocatechin gallate. The catechin preferably contains at least one species selected from the above catechin species. The catechin of the present invention is preferably a non-polymer species.

Generally, the catechin employed in the present invention may be obtained through direct extraction of tea leaves or through concentrating or purifying the tea leaf extract. Alternatively, the catechin may be produced from other materials or may be a column-purified product or a chemically synthesized product.

In one embodiment of extraction of catechin from tea leaves, water or hot water, optionally containing an extraction aid, was added to a processed tea leaf derived from tea leaf belonging to the genus *Camellia* (e.g., *C. sinensis* or *C. assamica* or a hybrid thereof) to prepare a tea extract. The extraction may be performed in a non-oxidizing atmosphere during which dissolved oxygen was removed through boiling deaeration or feeding an inert gas (e.g., nitrogen) thereto.

The processed tea leaf includes (1) green teas such as Sen-cha, Ban-cha, Gyokuro, Ten-cha, and kamairi-cha; (2) semi-fermented teas which are so-called oolong teas, such as Ti guan yin, Sezhong, Huang jin gui, and Wu yi yan cha; and (3) fermented teas called black teas such as Darjeeling, Uva and Keemun.

Examples of the extraction aid include organic acids and salts thereof such as sodium ascorbate.

The tea extract concentrate may be produced through concentration of the above-described extract, or the tea extract may be purified by use of a solvent or by means of a column. The concentrated or purified tea extract may be in the form of solid, aqueous solution, slurry, etc.

For example, the tea extract (also called tea catechin) may be prepared through methods disclosed in detail in, for example, JP-A-S59-219384, JP-A-H4-20589, JP-A-H5-260907, and JP-A-H5-306279. The tea extract may be a commercial product. Examples of the commercial product include POLYPHENON (product of Mitsui Norin Co., Ltd.), Teaflan (product of Ito En Ltd.), Sunphenon (product of Taiyo Kagaku Co., Ltd.), Teavigo (product of DSM Nutritional Products), and Sunoolong (product of Suntory Limited).

The catechins contained in the tea extract are present in the form of non-polymer species which is dissolved in the liquid, or in the form of solid which is adsorbed or included by tea micropowder suspended in the liquid.

The catechin content in the extract is 10 to 100 masse, preferably 30 to 95 mass %, more preferably 40 to 80 mass %. The ratio of the amount of catechin to the total amount of polyphenols contained in the tea extract is 10 mass % or higher immediately after production, preferably 20 mass % or higher.

For more effectively preventing decrease in physical functions accompanying senescence such as decrease in physical endurance, fatigue, decrease in energy metabolism, and dysfunction of mitochondria; muscle dysfunction; muscular atrophy; muscle senescence; etc., the ratio of the amount of one or more species selected from among gallocatechin, epigallocatechin, catechin gallate, epicatechin gallate, gallocatechin gallate, and epigallocatechin gallate to the total amount of catechins contained in the tea extract is preferably 40% or more, more preferably 60% or more, and even more preferably 80% or more.

Most of the catechins contained in tea leaves are in the form of epi-catechin. The epi-catechin can be transformed into the corresponding non-epi-catechin, which is a stereo-isomer, through treatment with heat, acid, alkali, etc. Thus, when a non-epi-catechin is employed, an extract of green tea, semi-fermented tea or fermented tea, or a concentrate thereof is dissolved in water, and the aqueous solution is heated, for example, at 40 to 140° C. for 0.1 minutes to 120 hours, to thereby obtain a non-epi-catechin. Alternatively, a concentrated tea extract having high non-epi-catechin content may also be employed. Epi-catechins and non-epicatechins may be used singly or in combination.

When (a) a catechin and (b) an amino acid selected from a branched-chain amino acid and taurine are employed in combination, an action on inhibiting decrease in muscle force accompanying senescence, a muscular atrophy inhibitory action, a motor function improvement action, and an action on preventing a bedridden state can be synergistically enhanced.

The branched-chain amino acid is an amino acid having a branched chain in the structure thereof. Among branched-chain amino acids, leucine, isoleucine, and valine are preferred.

In the present invention, preferably, at least one species selected from among valine, leucine, isoleucine, and taurine is employed in combination with a catechin.

Isomers of the amino acid (b) which may be employed include L-form, D-form, and DL-form. Among them, L-form is preferred since it is a naturally occurring species.

The amino acid (b) may be a commercial product or may be produced through a known method.

As described in the Examples hereinbelow, decrease in limit of running time, decrease in average oxygen consumption (energy consumption) and mitochondrial dysfunction, which accompany senescence, can be inhibited in senescence-accelerated model mice (SAM-P1) which consumed the tea extract. Therefore, a catechin can be used as a senescence inhibitor and a mitochondrial function-improving agent having a senescence inhibitory action, such as, specifically, inhibitory actions on decrease in physical endurance, fatigue, decrease in energy metabolism, dysfunction of mitochondria, etc. accompanying senescence. Also, a catechin can be used in the production of a senescence inhibitor and other similar agents. In another embodiment, the senescence inhibitor and similar agents containing a catechin as an effective ingredient can be used as a drug or a food or beverage for human and animals, exhibiting a senescence inhibitory effect, a mitochondrial function improvement effect, etc. When the agents are used as a food or beverage, there can be provided foods and beverages such as functional foods, sick diets, and foods for specified health uses, which are consumed for inhibition of dysfunctions accompanying senescence such as decrease in physical endurance, fatigue, decrease in energy metabolism, dysfunction of mitochondria, etc. The senescence inhibitor and other agents are highly effective for people on bed rest, aged people, and people lacking sufficient physical exercise, who tend to exhibit decrease in physical endurance, accumulation of fatigue, decrease in energy metabolism and dysfunction of mitochondria accompanying senescence.

Through intake of a tea extract by mice under motion-restricted conditions such as tenotomy and tail suspension, reduction of muscle mass and decrease in maximum muscle force have been inhibited. Thus, a catechin can be used as a muscle dysfunction inhibitor and a muscular atrophy inhibitor which have an inhibitory action on muscle dysfunction such as a muscular atrophy inhibitory action or a muscle dysfunction inhibitory action caused under motion-restricted conditions, or as an agent for preventing a bedridden state caused by disuse muscular atrophy or sarcopenia. A catechin may also be used in the production of the muscle dysfunction inhibitor and other similar agents. The muscle dysfunction inhibitor and similar agents containing a catechin as an effective ingredient are useful as drugs and foods and beverages for human and animals, exhibiting inhibitory effects on muscular atrophy and muscle dysfunction caused by aging, lack or reduction of exercise in life under motion-restricted conditions such as bed rest, fixation by a cast and desk works, or reduction in loading of physical activity to the body. When the agents are used as a food or beverage, there can be provided foods and beverages which have physiological functions (inhibition of muscular atrophy and muscle dysfunction and preventing a bedridden state) and are labeled with the relevant purposes. Such food or beverage can be applied to foods and beverages for specified uses (e.g., sick diets, foods for aged people, and foods for specified health uses), and functional foods.

Through intake of (a) a catechin and (b) an amino acid selected from a branched-chain amino acid and taurine in combination by mice of senescence-accelerated model (SAM-P1), improvement of motor function and a muscular atrophy inhibitory effect can be attained more remarkable, as compared with solo intake of (a) a catechin or (b) the amino acid. Thus, such a composition can be used as a muscle senescence inhibitor, a motor function-improving agent or an agent for preventing a bedridden state, which inhibits muscle dysfunction, muscular atrophy or prevents a bedridden state of people on bed rest, aged people or those lacking sufficient physical exercise. The composition can also be used to cope with muscle senescence of non-limited people, and used for the production of the muscle senescence inhibitor, motor function-improving agent or agent for preventing a bedridden state. The muscle senescence inhibitor, motor function-improving agent or agent for preventing a bedridden state can be used as a drug, quasi-drug or food or beverage for human and animals, by virtue of the effects thereof.

When the senescence inhibitor, mitochondrial function-improving agent, muscle dysfunction inhibitor, muscular atrophy inhibitor, agent for preventing a bedridden state, muscle senescence inhibitor, and motor function-improving agent of the present invention are employed as drugs, a variety of dosage forms are acceptable. Examples of the dosage form for peroral administration include solid forms such as tablet, capsule, granules and powder; and liquids such as syrup, elixir and enteral or tubal nutrient. Examples of the dosage form for parenteral administration include injections, suppositories, inhalations, percutaneous-absorbing agents, and external agents. Among them, peroral administration is preferred.

If desired, the muscle senescence inhibitor, motor function-improving agent or agent for preventing a bedridden state containing (a) a catechin and (b) an amino acid selected from a branched-chain amino acid and taurine may further contains auxiliary ingredients other than the essential ingredient. The additional auxiliary ingredients are those acceptable for and generally incorporated into drugs, quasi-drugs, and foods and beverages such as an amino acid, a vitamin, a dipeptide (e.g., carnosine) and an inorganic salt. Examples of the amino acid include arginine, glycine, lysine, alanine, cystine, cysteine, thianine and methionine.

For preparing such pharmaceutical products having a variety of dosage forms, the catechin or the catechin and the aforementioned amino acid of the invention may be used in combination with an appropriate pharmacologically acceptable carrier such as an excipient, a binder, a bulking agent, a disintegrant, a surfactant, a lubricant, a dispersant, a buffer, a preservative, a flavoring agent, a perfume, a coating agent, a vehicle or a diluting agent.

Examples of the excipient include solid powder carriers such as sugars (e.g., glucose, lactose, and sucrose), amino acids (e.g., glycine), and cellulose. Examples of the lubricant include silicon dioxide, talc, magnesium stearate, and polyethylene glycol. Examples of the binder include starch, gelatin, methylcellulose, and polyvinylpyrrolidone. Examples of the disintegrant include starch and agar.

When used in a food or beverage, the senescence inhibitor, mitochondrial function-improving agent, muscle dysfunction inhibitor, muscular atrophy inhibitor, agent for preventing a bedridden state, muscle senescence inhibitor or motor function-improving agent of the present invention may be incorporated into, for example, dairy foods such as cheese (natural and processed), ice cream, and yogurt; a sauce, soup, fish/meat flour (furikake), Japanese cakes (e.g., Senbei), western snack food (e.g., potato chips, pudding, jelly, gummy candy, candy, drops, caramel, chocolate and chewing gum), baked cakes (e.g., sponge cake, cakes, doughnuts, biscuits, cookies and crackers) and various beverages.

In one embodiment of production of foods and beverages, a catechin, or a catechin and the amino acid are used with various materials employed in general foods and beverages to process with a commonly used method.

When used in beverages, a catechin and the amino acid may be added to any type of beverages such as carbonated drinks (soft drinks), non-carbonated drinks (e.g., fruit juice, nectar, vegetable juice), refreshing beverages, sport beverages, near-water, diet beverages, tea, coffee, cocoa, and alcoholic beverages. The thus-prepared beverages may be mixed with other beverage ingredients, to thereby provide a wider range of beverages.

For example, a non-purified tea catechin containing insoluble matter such as micro-powdered tea leaves can be intentionally added to a beverage that has a colored and clear appearance which is stable during long-term storage, to thereby prepare a catechin-suspended beverage.

The aforementioned beverages are preferably provided as container-packed beverages. Examples of such container-packed beverages include a non-tea-based container-packed beverage (disclosed in Japanese Patent No. 3742094) and a tea-based container-packed beverage (disclosed in JP-A-2002-272373). Formulation examples will next be described.

From the viewpoints of taste and stability suitable for long-term consumption and effects of catechin, the container-packed beverages contain catechins ((A) non-epi-catechin and (B) epi-catechin), which are non-polymer species and dissolved in water, in a total amount of 50 to 2,500 mg based on 500 mL of beverage, preferably 200 to 2,500 mg, more preferably 300 to 1,300 mg, even more preferably 400 to 1,000 mg, from the viewpoint of taste.

The ratio of the amount of catechin to the total amount of polyphenol in the beverage is 10 wt. % or higher immediately after production, preferably 20 wt. % or higher.

An exemplary formulation in the case where a muscular atrophy inhibitor or a muscle dysfunction inhibitor is incorporated into a container-packed beverage will be described hereinbelow.

The container-packed beverage contains (A) non-epi-catechin and (B) epi-catechin which are non-polymer species and dissolved in water. Based on the beverage (500 mL), the total amount of (A) is 5 to 2,250 mg, the total amount of (A) and (B) is 50 to 2,500 mg, and the ratio by mass (A)/(B) is 0.1 to 9.0.

The total amount of (A) non-epi-catechin and (B) epi-catechin contained in the beverage (500 mL) is 50 to 2,500 mg. The total amount is preferably 460 to 2,500 mg, more preferably 500 to 1,300 mg, even more preferably 600 to 1,300 mg, even more preferably 640 to 800 mg, from the viewpoint of taste.

The component (A) is contained in the beverage (500 mL) in an amount of 5 to 2,250 mg, preferably 90 to 2,250 mg, more preferably 140 to 2,250 mg, even more preferably 140 to 1,880 mg, from the viewpoint of stability.

The ratio of the amount of catechin to the total amount of polyphenol in the beverage is 10 mass % or higher immediately after production, preferably 20 mass % or higher.

The ratio by mass of component (A)/component (B) is 0.1 to 9.0, preferably 0.25 to 9.0, more preferably 0.43 to 5.67, even more preferably 0.67 to 5.67, from the viewpoints of taste and stability.

A portion (30 to 98 wt. %, preferably 40 to 90 wt. %) of the catechins is preferably selected from among epigallocatechin gallate, gallocatechin gallate, epigallocatechin, and gallocatechin. In this case, the beverage is very tasty, and a long-lasting astringent taste is reduced, which is preferred. The beverage contains at least one species selected from among epigallocatechin gallate, gallocatechin gallate, epigallocatechin, and gallocatechin. However, the beverage generally contains all of the above catechin species.

When the muscle senescence inhibitor, motor function-improving agent, or agent for preventing a bedridden state containing (a) a catechin and (b) an amino acid selected from a branched-chain amino acid and taurine is incorporated into a container-packed beverage, in addition to catechin (a), the amino acid (b) may be incorporated in a total amount of 100 to 60,000 mg based on the beverage (500 mL). The total amount is preferably 500 to 20,000 mg, more preferably 500 to 10,000 mg, even more preferably 1,000 to 6,000 mg.

For the preferred amounts of amino acids, the leucine content in the beverage (500 mL) is preferably 100 mg to 20,000 mg, more preferably 500 to 4,000 mg; the isoleucine content is preferably 100 mg to 20,000 mg, more preferably 500 to 3,000 mg; the valine content is preferably 100 mg to 20,000 mg, more preferably 500 to 3,000 mg; and the taurine content is preferably 100 mg to 10,000 mg, more preferably 500 to 3,000 mg.

The beverage has a pH (25° C.) of 3 to 7, preferably 4 to 7, more preferably 5 to 7, from the viewpoints of taste and chemical stability of catechins.

To the aforementioned beverages, an additional component which can be used with a catechin or a mixture of a catechin and the amino acid may be added. Examples of such an additive include an anti-oxidant, a flavoring agent, an ester, an organic acid, an organic acid salt, an inorganic acid, an inorganic acid salt, an inorganic salt, a dye, an emulsifier, a preservative, a seasoning agent, a sweetener, a sour agent, a fruit extract, a vegetable extract, a pollen load extract, a pH-adjuster, and a quality-stabilizer. These additives may be used singly or in combination.

The container used for receiving the beverages can be a molded container formed mainly of polyethylene terephthalate (a so-called PET bottle) which is widely employed for general beverages. Also, generally employed containers such as a metal can, a paper composite container with metal foil or plastic film, and a bottle may also be used for providing the beverages. The term "beverage(s)" employed herein refers to a beverage which can be drunk without dilution.

When the container is formed of a material (e.g., metal can) which allows heat sterilization after packing of the beverage, the beverage filled in the container is sterilized under the conditions as stipulated by the Food Sanitation Law. When a containers which cannot be subjected to retort sterilization such as a PET bottle or a paper container is employed, in one possible procedure, the beverage is sterilized at high temperature for a short time under the same conditions as employed above by means of, for example, a plate heat-exchanger, then cooled to a predetermined temperature before, and filled into the container. Alternatively, to the container in which a content is placed under sterilized conditions, other ingredients may be added. Yet alternatively, the content heat-sterilized under acidic conditions may be returned to a neutral pH under sterilized conditions, or the content heat-sterilized under neutral conditions may be returned to an acidic pH under sterilized conditions.

Examples of the sick diet include enteral nutrients and thick liquid diets (foods), which are administered to aged patients or bed-rest patients who encounter difficulty in taking an appropriate amount of nutrients.

Enteral nutrients and thick liquid diets may be produced through a method in the art by adding nutrient ingredients to a catechin, or a mixture of a catechin and the amino acid. Specifically, a catechin and various materials are dissolved in an appropriate solvent with mixing, and the liquid is homogenized by means of, for example, a homogenizer, then filled in a container (e.g., a retort or a plastic container), followed by a known sterilization process, whereby liquid, semi-solid, and solid pharmaceutical products can be produced. Alternatively, when the mixture homogenized by means of, for example, a homogenizer is subjected to a known spray drying method or a similar method, powder-form pharmaceutical products can be produced.

An example of the nutrient composition is a nutrient composition containing protein, sugar, fat, trace elements, vitamins, an emulsifier, a flavoring agent, etc. Examples of the protein source include proteins such as milk protein, soybean protein, and ovalbumin, which have high nutritive value with good amino acid balance. A degradation product thereof, egg-white oligopeptide, soybean hydrolyzate, etc. may also be used. A mixture of amino acids may be used.

The nutrient composition is preferably administered at a daily dose of 10 to 50 kcal/body weight-kg for an adult (as converted to calories of a nutrient).

The content of catechin in the aforementioned senescence inhibitor, mitochondrial function-improving agent, muscle dysfunction inhibitor, muscular atrophy inhibitor or agent for preventing a bedridden state, which varies depending on applications, is generally 0.01 to 5 mass %, preferably 0.05 to 5 mass %, more preferably 0.1 to 1 mass % in the case of foods, beverages and pet foods. In the cases of pharmaceutical products other than those mentioned above (e.g., oral solid pharmaceutical products such as tablets, granules, and capsules; and oral liquid pharmaceutical products such as oral liquid and syrup), the catechin content is generally 0.01 to 95 mass %, preferably 5 to 90 mass %, more preferably 5 to 95 mass %, even more preferably 10 to 80 mass %, even more preferably 10 to 95 mass %.

When the muscle senescence inhibitor, motor function-improving agent or agent for preventing a bedridden state containing (a) a catechin and (b) an amino acid selected from a branched-chain amino acid and taurine is used as a non-beverage product, the catechin (a) content, which varies depending on applications, is generally 0.01 to 5 wt. %, preferably 0.05 to 5 wt. %, more preferably 0.1 to 1 wt. % in the case of foods and pet foods. In the cases of pharmaceutical products other than those mentioned above (e.g., oral solid pharmaceutical products such as tablets, granules, and capsules; and oral liquid pharmaceutical products such as oral liquid and syrup), the catechin content is generally 0.01 to 95 wt. %, preferably 5 to 90 wt. %, more preferably 10 to 80 wt. %.

The amount of the amino acid (b) contained in each of the non-beverage products, which varies depending on applications, is generally 0.01 to 5 wt. %, preferably 0.1 to 5 wt. %, more preferably 0.2 to 2 wt. % in the case of foods and pet foods. In the cases of pharmaceutical products other than those mentioned above (e.g., oral solid pharmaceutical products such as tablets, granules, and capsules; and oral liquid pharmaceutical products such as oral liquid and syrup), the amino acid content is generally 0.01 to 95 wt. %, preferably 5 to 90 wt. %, more preferably 10 to 80 wt. %.

The daily dose (effective dose) of the senescence inhibitor, mitochondrial function-improving agent, muscle dysfunction inhibitor, muscular atrophy inhibitor, agent for preventing a bedridden state, muscle senescence inhibitor or motor function-improving agent of the present invention, which varies depending on the sex, age, body weight, gravity of the symptom, etc. of the patient to which the agents are administered, is preferably 100 to 3,000 mg/60-kg-body weight for an adult (as an amount of catechin), more preferably 250 to 2,000 mg/60-kg-body weight, even more preferably 250 to 1,000 mg/60-kg-body weight.

In the muscle senescence inhibitor, motor function-improving agent, or agent for preventing a bedridden state containing (a) a catechin and (b) an amino acid selected from a branched-chain amino acid and taurine, the daily dose of the amino acid (b) is preferably 100 to 60,000 mg/60-kg-body weight, more preferably 500 to 20,000 mg/60-kg-body weight, even more preferably 1,000 to 6,000 mg/60-kg-body weight. The catechin and the amino acid may be administered separately or simultaneously, so long as a synergistic effect of these components can be attained.

The present invention will be described hereinafter in detail by way of Test Examples employing compositions falling within the scope of the present invention, followed by Preparation Examples of the compositions described as Examples.

EXAMPLES

Test Example 1

Senescence Inhibition Effect of Catechins

In Test Example 1, a green tea extract having a total catechin content of 81% was employed as tea catechin.

The composition of catechins contained in the tea catechin was determined through a known method (see, for example, JP-A-2006-129738), which was as follows: gallocatechin (7%), gallocatechin gallate (4%), epicatechin (9%), epigallocatechin (23%), epicatechin gallate (12%), epigallocatechin gallate (41%), and other species (4%).

(1) Preparation of Mice of Experiment Groups

13 Week-old SAM-P1 male mice (mice of senescence-accelerated model) and SAM-R1 male mice (normally senescent mice) were individually bred for 5 weeks for adaptation. Thereafter, these mice were conditioned by running on a treadmill, and the running time to exhaustion of each mouse was measured.

Specifically, a mouse was allowed to rest on a standstill treadmill and was conditioned to the test environment. Thereafter, the treadmill was activated at a certain speed. The point in time at which rotation of the treadmill started was taken as the start of running. The belt speed (m/min) was changed at predetermined intervals. The point in time at which the mouse could no longer run was regarded as the end of running. The duration from the start of running to the end of running was employed as a running time to exhaustion, which served as an index of physical endurance.

The belt speed profile during measurement of running time to exhaustion of mice was as follows: 10 m/min at the beginning; 10 m/min for 5 min; 15 m/min for 5 min; 20 m/min for 60 min; 22 m/min for 60 min; 24 m/min for 60 min; 26 m/min for 60 min; and 28 m/min (to the end).

The test mice were divided into the following groups (eight mice in each group): SAM-R1 (normally senescent mice) control group, SAM-P1 (mice of senescence-accelerated model) control group, and SAM-P1 catechin group, such that there was no difference in running time to exhaustion between groups.

(2) Effect of Tea Catechin on Mice of Senescence-Accelerated Model

A control diet containing no tea catechin and a catechin-containing diet having compositions shown in Table 1 were prepared.

The SAM-R1 control group and the SAM-P1 control group were both fed on the control diet, and the SAM-P1 catechin group was fed on the catechin-containing diet. The mice of these groups were bred for 10 weeks.

The mice of each group were subjected to physical exercise at 15 m/min for 30 minutes three times per week.

TABLE 1

| Diet composition (wt. %) | | |
|---|---|---|
| | Control diet | Catechin-containing diet |
| Casein | 20% | 20% |
| DL-methionine | 0.2% | 0.2% |
| Vegetable oil | 10% | 10% |
| Potato starch | 55.5% | 55.15% |
| Cellulose | 8.1% | 8.1% |
| Minerals | 4% | 4% |
| Vitamins | 2.2% | 2.2% |
| Tea extract (Tea catechin) | 0 | 0.35% |
| Total | 100% | 100% |

After breeding for eight weeks, the running time to exhaustion of each group was determined. Table 2 shows the determined running time to exhaustions of mice.

TABLE 2

| Running time to exhaustion of mice after breeding for 8 weeks | | |
|---|---|---|
| | Running time to exhaustion (min) before test | Running time to exhaustion (min) after breeding for 8 weeks |
| SAM-R1 control group | 140.0 ± 3.6 | 154.8 ± 9.3* |
| SAM-P1 control group | 120.7 ± 7.5 | 100.0 ± 5.8 |
| SAM-P1 catechin group | 120.1 ± 7.8 | 121.4 ± 7.1* |

Statistically significant to SAM-P1 control group: *P < 0.05

After breeding for nine weeks, the oxygen consumption (energy consumption) of the mice of each group at rest was determined by analyzing respiratory gas. The respiratory gas was analyzed with an Oxymax system (product of Columbus) with 8-serial chamber. Each mouse was placed in the chamber and allowed to rest for 6 hours. Subsequently, the average oxygen consumption (24 hours) (oxygen consumption (mL)/kg-body weight of mouse/min (mL/kg/min)) was measured for two minutes continuously every 18 minutes. Table 3 shows the average oxygen consumption (24 hours) (mL/kg/min).

TABLE 3

| Average oxygen consumption (energy consumption) (24 hours) of mice after breeding for 9 weeks | |
|---|---|
| | After breeding for 9 weeks Oxygen consumption (mL/kg/min) |
| SAM-R1 control group | 53.2 ± 1.8* |
| SAM-P1 control group | 46.9 ± 1.3 |
| SAM-P1 catechin group | 51.0 ± 0.9* |

Statistically significant to SAM-P1 control group: *P < 0.05

As shown in Table 2, the SAM-P1 (mice of senescence-accelerated model) control group exhibited a running time to exhaustion that was significantly shorter than that of the SAM-R1 (normally senescent mice) control group, indicating that physical endurance of mice decreased accompanying senescence.

In contrast, the SAM-P1 catechin group (mice which were given the catechin-containing diet) exhibited a running time to exhaustion that was significantly longer than that of the SAM-P1 control group, indicating that intake of tea catechin suppressed a senescence-related decrease of physical endurance and provided resistance to fatigue.

The running time to exhaustion of the SAM-P1 (mice of senescence-accelerated model) control group was shortened by about 20 minutes after breeding for 8 weeks, as compared with that measured before the test.

No reduction of running time to exhaustion was observed for the SAM-P1 catechin group (mice which were given the catechin-containing diet), indicating that intake of tea catechin suppressed a senescence-related decrease of physical endurance.

As shown in Table 3, the SAM-P1 (mice of senescence-accelerated model) control group exhibited an oxygen consumption (energy consumption) that was significantly lower than that of the SAM-R1 (normally senescent mice) control group, indicating that the oxygen consumption of mice decreased due to senescence, resulting in a reduction in energy metabolism.

In contrast, the oxygen consumption of the mice which had taken the catechin diet was significantly high with respect to the SAM-P1 control group, indicating that tea catechin suppressed a reduction in energy metabolism accompanying senescence.

Prolongation of the running time and increase of oxygen consumption through intake of tea catechin indicates that fatigue is prevented by tea catechin.

Test Example 2

Inhibition Effect of Catechins on Mitochondrial Dysfunction (1) Preparation of Mice of Experiment Groups 13 Week-old SAM-P1 male mice (mice of senescence-accelerated model) and SAM-R1 male mice (normally senescent mice) were individually bred for 5 weeks for adaptation.

Thereafter, these mice were conditioned by running on a treadmill, and the running time to exhaustion of each mouse was measured.

Specifically, a mouse was allowed to rest on a standstill treadmill and was conditioned to the test environment. Thereafter, the treadmill was activated at a certain speed. The point in time at which rotation of the treadmill started was taken as the start of running. The belt speed (m/min) was changed at predetermined intervals. The point in time at which the mouse could no longer run was regarded as the end of running. The duration from the start of running to the end of running was employed as a running time to exhaustion, which served as an index of physical endurance.

The belt speed profile during measurement of running time to exhaustion of mice was as follows: 10 m/min at the beginning; 10 m/min for 5 min; 15 m/min for 5 min; 20 m/min for 60 min; 22 m/min for 60 min; 24 m/min for 60 min; 26 m/min for 60 min; and 28 m/min (to the end).

The test mice were divided into the following groups (eight mice in each group): SAM-R1 (normally senescent mice) control group, SAM-P1 (mice of senescence-accelerated model) control group, SAM-P1 catechin group, SAM-P1 physical exercise group, and SAM-P1 catechin/physical exercise combination group, such that there was no difference in running time to exhaustion between groups.

(2) Effect of Tea Catechin on Mice of Senescence-Accelerated Model

A control diet containing no tea catechin and a catechin-containing diet having compositions shown in Table 4 were prepared.

The SAM-R1 control group, the SAM-P1 control group, and the SAM-P1 physical exercise group were fed on the control diet, and the SAM-P1 catechin group and the SAM-P1 catechin/physical exercise combination group were both fed on the catechin-containing diet. The mice of these groups were bred for 10 weeks.

The mice of each group were subjected to a physical exercise at 15 m/min for 30 minutes three times per week.

TABLE 4

| Diet composition (wt. %) | | |
|---|---|---|
| | Control diet | Catechin-containing diet |
| Casein | 20% | 20% |
| DL-methionine | 0.2% | 0.2% |
| Vegetable oil | 10% | 10% |
| Potato starch | 55.5% | 55.15% |
| Cellulose | 8.1% | 8.1% |
| Minerals | 4% | 4% |
| Vitamins | 2.2% | 2.2% |
| Tea extract (Tea catechin) | 0 | 0.35% |
| Total | 100% | 100% |

After breeding for 10 weeks, a gastrocnemius muscle was removed from each mouse of the groups, and RNA samples were obtained by use of ISOGEN (product of Nippon Gene). Each RNA sample was quantitated and subjected to reverse transcription by use of Super Script First-Strand Synthesis System for RT-PCR (product of Invitrogen) such that the amount of RNA per reaction was adjusted to 5 μg, to thereby produce cDNA. Reverse transcription reaction was performed at 42° C. for 50 minutes and 70° C. for 15 minutes.

The thus-prepared cDNA was 40-fold diluted (for unknown samples) or 10-fold diluted (for standard sample), and each diluted sample was subjected to quantitative PCR by means of an ABI PRISM 7700 Sequence Detector (product of Applied Biosystems). The relative mRNA expression amount was obtained through correction based on the amount of 36B4 mRNA expression as a standard.

The following primers were employed: GenBank: X57780, nt876-897, and nt957-976 (COX1); AF37780, nt488-507, and nt567-588 (COX2), NC_005089, nt9196-9217, and nt9308-9327 (COX3); NM_053091, nt276-295, and nt396-415 (COX4); NM_010479, nt1815-1835, and nt1916-1937 (heat shock protein 72 (HSP72)); NM_008904, nt642-661, and nt751-770 (PGC-1α); and NM_133249, nt2865-2885, and nt2945-2965 (PGC-1β).

The results are shown in Table 5.

TABLE 5

| Gene expression in mouse gastrocnemius muscle after breeding for 10 weeks | | | | | |
|---|---|---|---|---|---|
| | SAM-R1 control group | SAM-P1 control group | SAM-P1 catechin group | SAM-P1 physical exercise group | SAM-P1 combination group |
| COX1 | 127 ± 6* | 100 ± 7 | 107 ± 7 | 118 ± 5 | 117 ± 5 |
| COX2 | 140 ± 5* | 100 ± 5 | 102 ± 4 | 114 ± 3 | 126 ± 7* |
| COX3 | 139 ± 6* | 100 ± 7 | 107 ± 4 | 118 ± 5* | 125 ± 5* |
| COX4 | 160 ± 7* | 100 ± 7 | 111 ± 3 | 126 ± 3* | 141 ± 2* |
| HSP72 | 147 ± 8* | 100 ± 5 | 107 ± 4 | 122 ± 5* | 129 ± 7* |
| PGC-1α | 146 ± 10* | 100 ± 9 | 113 ± 6 | 118 ± 7 | 124 ± 4* |
| PGC-1β | 123 ± 4* | 100 ± 3 | 104 ± 3 | 106 ± 6 | 113 ± 3* |

Statistically significant to SAM-P1 control group: *P < 0.05

As shown in Table 5, gene expression of COX1 to COX4, HSP72, PGC-1α, and PGC-1β in gastrocnemius muscle of the SAM-P1 (mice of senescence-accelerated model) control group was significantly low with respect to that of the SAM-R1 (normally senescent mice) control group, indicating that expression of a gene related to electron transport system and that of a gene related to differentiation and proliferation of mitochondria were reduced accompanying senescence.

In contrast, gene expression of COX2 to COX4 and HSP72 of the SAM-P1 catechin/physical exercise combination group was significantly high with respect to that of the SAM-P1 control group, indicating that intake of tea catechin suppressed reduction of expression of a gene related to electron transport system and a gene related to differentiation and proliferation of mitochondria accompanying senescence.

In addition, the fact that combination of intake of tea catechin and physical exercise suppressed a gene related to electron transport system indicates that the mitochondrial function was maintained.

As described above, catechins can have a senescence inhibition action, specifically, catechins have an action on suppressing decrease in physical endurance, fatigue, decrease in energy metabolism, dysfunction of mitochondria, etc. accompanying senescence. Therefore, catechins are useful senescence inhibitors and mitochondrial function-improving agents.

Test Example 3

Effects of Catechins on Muscular Atrophy Inhibition and on Muscle Dysfunction Inhibition In Test Example 3, a green tea extract having a total catechin content of 81% was employed. The compositions of the catechin were as follows: gallocatechin (7%), gallocatechin gallate (4%), epicatechin (9%), epigallocatechin (23%), epicatechin gallate (12%), epigallocatechin gallate (41%), and other species (4%).

(1) Efficacy of Catechins on Tenotomy Mice

Male Balb/c mice (9 weeks old) were subjected to preliminary breeding for one week and divided into three groups (non-treated group, control group, and catechin group) on the basis of the body weight (each group: n=8). Thereafter, mice of these groups were given diets having compositions shown in Table 6 for two weeks.

TABLE 6

| Diet composition (wt. %) | | |
|---|---|---|
| | Non-treated group/ control group | Catechin group |
| Casein | 20 | 20 |
| DL-methionine | 0.2 | 0.2 |
| Fats/oils | 10 | 10 |
| α-Potato starch | 55.5 | 55 |
| Cellulose | 8.1 | 8.1 |
| Minerals | 4 | 4 |
| Vitamins | 2.2 | 2.2 |
| Catechin formulation | | 0.5 |
| Total | 100 | 100 |

After feeding of the above diets for two weeks, mice of the control group and those of the catechin group were subjected to achillotenotomy of hindlimbs, to thereby remove tension of muscles belonging to the hindlimb calf (e.g., soleus muscle). Generally, a muscle relieved from tension exhibits disuse muscular atrophy, and reduction in muscle mass and muscle force. Mice of the non-treated group were not subjected to tenotomy.

Sthenometry of Removed Muscle

Figure 2:
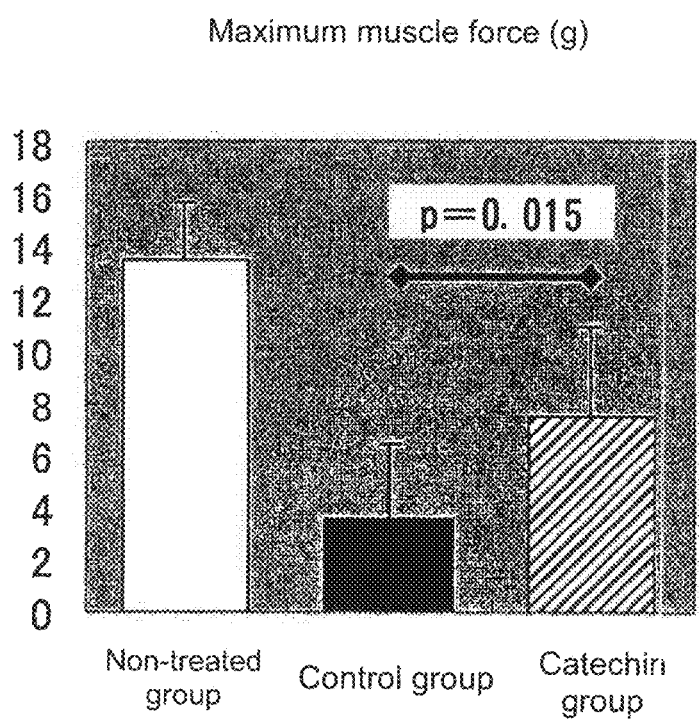
FIG. 2
A graph showing maximum muscle force (g) of a control group and a catechin group treated with tenotomy, and a non-treated group.

Two weeks after tenotomy, mice were continuously bred with the test diets. A soleus muscle was removed from a mouse of each group through dissection and fixed to a transducer (WPI: FORT100) in Krebs solution of 37° C. (aeration: 95%-oxygen, 5%-carbon dioxide). Subsequently, under electrical stimulation (0.2 msec, 40 Hz), the maximum muscle force of the muscle sample was determined. FIG. 1 shows the masses of soleus muscle in a wet state, and FIG. 2 shows the results of muscle force measurement.

(2) Efficacy of Catechins on Tail-Suspended Mice

Male Balb/c mice (9 weeks old) were subjected to preliminary breeding for one week and divided into three groups (non-treated group, control group, and catechin group) on the basis of the body weight (each group: n=8). Thereafter, mice of these groups were given diets having compositions shown in Table 6 for two weeks.

After feeding of the above diets for two weeks, mice of the control group and those of the catechin group were subjected to tail suspension, to thereby remove weight load of hindlimb muscles (e.g., soleus muscle). Generally, a muscle reduced weight-load exhibits disuse muscular atrophy, and muscle mass and muscle force decrease. Mice of the non-treated group were not subjected to tail suspension.

Sthenometry of Removed Muscle

Figure 3:
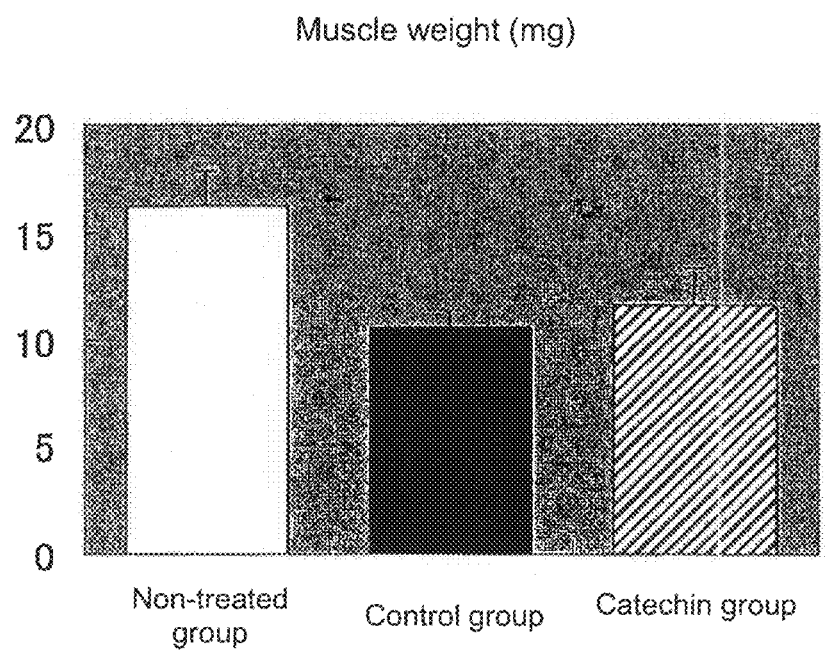
FIG. 3
A graph showing masses of soleus muscle (mg) of a control group and a catechin group treated with tail suspension, and a non-treated group.
Figure 4:
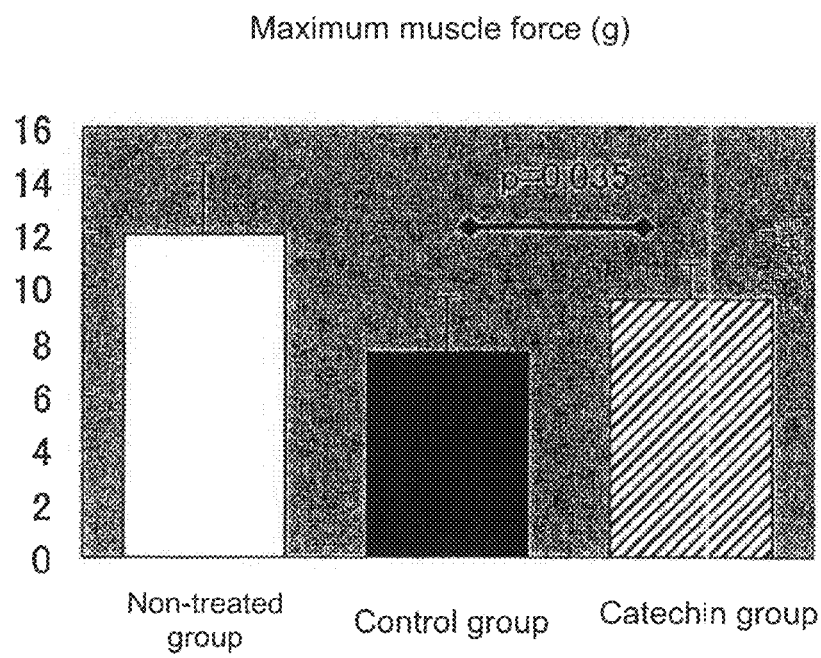
FIG. 4
A graph showing maximum muscle force (g) of a control group and a catechin group treated with tail suspension, and a non-treated group.

Ten days after tail suspension, mice were continuously bred with the test diets. A soleus muscle was removed from a mouse of each group through dissection and fixed to a transducer (WPI: FORT100) in Krebs solution of 37° C. (aeration: 95%-oxygen, 5%-carbon dioxide). Subsequently, under electrical stimulation (0.2 msec, 40 Hz), the maximum muscle force of the muscle sample was determined. FIG. 3 shows the masses of soleus muscle in a wet state, and FIG. 4 shows the results of muscle force measurement.

As shown in Test Example 3, intake of catechin suppressed muscular atrophy and muscle dysfunction. In Test Example 3, no substantial effect of catechin on enhancement of muscle mass and muscle force was observed before treatment. Therefore, catechins were found to have an inhibitory effect on muscular atrophy and a muscle dysfunction caused by decreased muscle activity. Thus, catechins are considered a useful agent for preventing a bedridden state or a muscle dysfunction inhibitor.

Test Example 4

Muscle Senescence Inhibitory Effect of a Mixture of (a) Catechin and (b) Amino Acid In Test Example 4, a green tea extract having a total catechin content of 81% was employed as (a) a catechin. The compositions of catechins were as follows: gallocatechin (7%), gallocatechin gallate (4%), epicatechin (9%), epigallocatechin (23%), epicatechin gallate (12%), epigallocatechin gallate (41%), and other species (4%). Leucine was used as (b) amino acid.

10 Week-old SAM-P1 male mice (mice of senescence-accelerated model) and SAM-R1 male mice (normally senescent mice) were individually for 5 weeks for adaptation. Thereafter, these mice were divided into the following groups (eight mice in each group): SAM-R1 control group, SAM-P1 control group, SAM-P1 catechin group, SAM-P1 leucine group, and SAM-P1 catechin/leucine combination group, such that there was no difference in body weight between groups. These mice were bred for nine weeks on diets having formulations shown in Table 7. The mice of each group were subjected to a physical exercise at 10 m/min for 3 minutes in a running-water pool five times a day and four days a week.

TABLE 7

| Diet composition (wt. %) | | | | |
|---|---|---|---|---|
| | Control group | Catechin group | Leucine group | Combination group |
| Casein | 20% | 20% | 19.65% | 19.65% |
| DL-methionine | 0.2% | 0.2% | 0.2% | 0.2% |
| Fats/oils | 10% | 10% | 10% | 10% |
| Potato starch | 55.5% | 55.15% | 55.5% | 55.15% |
| Cellulose | 8.1% | 8.1% | 8.1% | 8.1% |
| Minerals | 4% | 4% | 4% | 4% |
| Vitamins | 2.2% | 2.2% | 2.2% | 2.2% |
| Catechins | 0% | 0.35% | 0% | 0.35% |
| Leucine | 0% | 0% | 0.35% | 0.35% |
| Total | 100% | 100% | 100% | 100% |

After breeding for nine weeks, a soleus muscle was removed from a mouse of each group through dissection and fixed to a transducer (FORT100, product of World Precision Instruments, Inc.) in Krebs solution of 37° C. (aeration: 95%-oxygen, 5%-carbon dioxide). Subsequently, under electrical stimulation (0.5 msec, 140 Hz), the maximum muscle force of the muscle sample was determined. Table 8 shows the results of muscle force measurement.

TABLE 8

Maximum force of soleus muscle of mice under electrical stimulation after breeding for 9 weeks

| | After breeding for 9 weeks | |
| --- | --- | --- |
| | Maximum muscle force (g) | Statistical significance |
| SAM-R1 control group | 16.5 ± 1.4 | *p < 0.001 |
| SAM-P1 control group | 7.9 ± 1.2 | |
| SAM-P1 catechin group | 9.1 ± 1.1 | no significance |
| SAM-P1 leucine group | 11.1 ± 0.7 | no significance |
| SAM-P1 catechin/leucine combination group | 12.3 ± 0.9 | *p < 0.01 |

Statistically significant to SAM-P1 control group (Dunnet test)

As shown in Table 8, the maximum soleus muscle force of the SAM-P1 (mice of senescence-accelerated model) control group significantly decreased as compared with the SAM-R1 (normally senescent mice) control group, indicating that the maximum muscle force decreased accompanying senescence. No significant difference in the maximum soleus muscle force was observed between mice having taken a diet containing catechin or leucine and that of the SAM-P1 control group, but combined use of catechin and leucine was found to significantly inhibit a decrease in muscle force caused by senescence.

As described above, a combination of catechin and amino acid employed in the present invention is a useful inhibitor against muscle dysfunction due to senescence. In addition, since the catechin/leucine combination group exhibited an increase in muscle force as compared with the SAM-P1 control group, combined use of catechin and leucine is effective for enhancing motor function.

Test Example 5

Muscular Atrophy Inhibitory Effect of a Mixture of (a) Catechin and (b) Amino Acid In Test Example 5, a green tea extract having a total catechin content of 81% was employed as a catechin. The compositions of catechins were as follows: gallocatechin (7%), gallocatechin gallate (4%), epicatechin (9%), epigallocatechin (23%), epicatechin gallate (12%), epigallocatechin gallate (41%), and other species (4%). Leucine was used as an amino acid.

13 Week-old SAM-P1 male mice (mice of senescence-accelerated model) and SAM-R1 male mice (normally senescent mice) were separately bred for 5 weeks for preliminary breeding. Thereafter, these mice were divided into the following groups (eight mice in each group): SAM-R1 control group, SAM-P1 control group, and SAM-P1 catechin/leucine combination group, such that there was no difference in body weight between groups. These mice were bred for nine weeks on diets having formulations shown in Table 9. The mice of each group were subjected to a physical exercise at 10 m/min for 3 minutes in a running-water pool five times a day and four days a week.

TABLE 9

| Diet composition (wt. %) | | |
| --- | --- | --- |
| | Control group | Catechin/leucine combination group |
| Casein | 20% | 19.65% |
| DL-methionine | 0.2% | 0.2% |
| Fats/oils | 10% | 10% |

TABLE 9-continued

| Diet composition (wt. %) | | |
| --- | --- | --- |
| | Control group | Catechin/leucine combination group |
| Potato starch | 55.5% | 55.15% |
| Cellulose | 8.1% | 8.1% |
| Minerals | 4% | 4% |
| Vitamins | 2.2% | 2.2% |
| Catechins | 0% | 0.35% |
| Leucine | 0% | 0.35% |
| Total | 100% | 100% |

After breeding for nine weeks, gastrocnemius muscle, soleus muscle, plantar muscle, extensor digitorum longus muscle, and quadriceps muscle of thigh were removed from a mouse of each group through dissection and weighed, to thereby determine the total muscle weight. Table 10 shows the total muscle weight per body weight.

TABLE 10

Muscle weight per body weight of mice after breeding for 9 weeks (%)

| | After breeding for 9 weeks | |
| --- | --- | --- |
| | Muscle weight (%) | Statistical significance |
| SAM-R1 control group | 2.01 ± 0.06 | *p < 0.0001 |
| SAM-P1 control group | 1.59 ± 0.04 | |
| SAM-P1 catechin/leucine combination group | 1.82 ± 0.06 | *p < 0.01 |

Statistically significant to SAM-P1 control group (Dunnet test)

As shown in Table 10, the muscle weight per body weight of the SAM-P1 (mice of senescence-accelerated model) control group significantly decreased as compared with the SAM-R1 (normally senescent mice) control group, indicating that muscular atrophy was caused accompanying senescence. The muscle weight of the mice which were given a diet containing catechin and leucine was significantly larger than that of the SAM-P1 control group.

As described above, a combination of catechin and amino acid employed in the present invention is a useful inhibitor against muscular atrophy due to senescence.

Hereinafter, pharmaceutical production examples of the senescence inhibitor and other agents of the present invention will be described.

Pharmaceutical Production Example 1

Container-Packed Beverages for Senescence Inhibition

Container-packed beverages for senescence inhibition were prepared according to the formulation and preparation conditions shown in Table 11. The composition of the tea extracts (tea catechin) employed for producing the container-packed beverages is shown in Table 12. The thus-prepared beverages exhibited excellent storage stability and good taste.

TABLE 11

Formulation of tea beverages

|  | Green tea beverage | (g/100 mL) Oolong tea beverage |
|---|---|---|
| Green tea extract (g) | 17.5 | 0 |
| Oolong tea extract (g) | 0 | 8 |
| Tea extract (g) | 0.37 | 0.48 |
| Purified water (g) | balance | balance |
| Na ascorbate (g) | 0.05 | 0.05 |
| pH (after sterilization) | 5.98 | 5.87 |
| Sterilization temperature (° C.) | 133 | 134 |
| Heating time for sterilization (sec) | 30 | 30 |
| Container | PET container | PET container |

TABLE 12

Catechin compositions of beverages

|  | Green tea beverage | (mg/500 mL) Oolong tea beverage |
|---|---|---|
| Catechin | 32.4 | 30.7 |
| Epicatechin | 32.7 | 35.6 |
| Gallocatechin | 124.1 | 113.0 |
| Epigallocatechin | 85.8 | 91.8 |
| Catechin gallate | 23.0 | 22.1 |
| Epicatechin gallate | 37.3 | 41.9 |
| Gallocatechin gallate | 94.9 | 86.7 |
| Epigallocatechin gallate | 110.9 | 120.1 |
| Total non-polymer catechins | 541.0 | 541.9 |

Pharmaceutical Production Example 2

Enteral Nutrient for Senescence Inhibition (Thick Fluid Diet)

A pharmaceutical product falling within the scope of the invention having a formulation shown in Table 13 was placed in a retort, followed by sealing through a customary method. The retort was subjected to high-pressure steam sterilization, whereby an enteral nutrient was prepared. Minerals employed were in the form of a mixture of organic or inorganic salts of Na, K, Ca, Mg, P, Cl, Fe, etc., and vitamins employed were in the form of a mixture containing vitamins A, D, E, $B_1$, $B_2$, $B_6$, $B_{12}$, C, niacin, pantothenic acid, etc. These minerals and vitamins were employed in amounts according to the Japanese Recommended Dietary Allowance.

TABLE 13

Enteral nutrient formulation

|  | (g/100 mL) |
|---|---|
| Milk casein | 3.40 |
| Separated soybean protein | 1.67 |
| Dextrin | 14.86 |
| Sucrose | 1.30 |
| Soybean oil | 1.75 |
| *Perilla* oil | 0.18 |
| Soybean phospholipid | 0.14 |
| Glycerin fatty acid ester | 0.07 |
| Minerals | 0.60 |
| Vitamins | 0.06 |
| Tea catechin (Teaflan 90S, product of Ito En Ltd.) | 0.11 |
| Purified water | balance |

Pharmaceutical Production Example 3

Jerry for Senescence Inhibition

A gelling agent mixture of carageenan and locust bean gum (0.65%), grapefruit juice 50% concentrate (5.0%), citric acid (0.05%), vitamin C (0.05%), and tea catechin (Teavigo, product of DSM Nutritional Products) (0.54%) were mixed together, and water was added to the mixture so as to adjust the amount to 100%. The ingredients were dissolved at 65° C. A small amount of grapefruit flavor was added to the solution, and the resultant liquid was maintained at 85° C. for five minutes for sterilization. After sterilization, the liquid was dispensed to 100-mL containers. The dispensed products were allowed to stand for 8 hours to gradually cool to 5° C., thereby forming a catechin-containing jelly.

Pharmaceutical Production Example 4

Vitamin-Containing Oral Liquid for Senescence Inhibition

Taurine (800 mg), sucrose (2,000 mg), caramel (50 mg), sodium benzoate (30 mg), vitamin $B_1$ nitrate (5 mg), vitamin $B_2$ (20 mg), vitamin $B_6$ (20 mg), vitamin C (2,000 mg), vitamin E (100 mg), vitamin $D_3$ (2,000 IU), nicotinic acid amide (20 mg), and tea catechin (POLYPHENON 70S, product of Mitsui Norin Co., Ltd.) (100 mg) were added to a suitable amount of purified water, and the pH of the solution was adjusted to 3 by use of aqueous phosphoric acid solution. Purified water was further added to the solution, to thereby adjust the total volume to 50 mL. The mixture was sterilized at 80° C. for 30 minutes, whereby a catechin-containing vitamin oral liquid was produced.

Pharmaceutical Production Example 5

Chewable Tablets for Senescence Inhibition

Tablets, having a formulation of ascorbic acid (180 mg), citric acid (50 mg), aspartame (12 mg), magnesium stearate (24 mg), crystalline cellulose (120 mg), lactose (274 mg), and tea catechin (Teaflan 90S, product of Ito En Ltd.) (540 mg), were prepared in accordance with the Japanese Pharmacopoeia (General rules for preparations, "Tablets"), whereby catechin-containing chewable tablets were produced.

Pharmaceutical Production Example 6

Tablets for Senescence Inhibition

Catechin-containing tablets were prepared through a routine method, which have the following formulation (wt. %): tea catechin (POLYPHENON 70S, product of Mitsui Norin Co., Ltd.) (20), sodium malate (20), palatinose (20), ascorbic acid (20), Vitamin Mix (product of The Nippon Koryo Yakuhin Kaisha, Ltd.) (5), crystalline cellulose (5), sucrose ester (4), silicon dioxide (1), and eggshell-derived calcium (5).

Pharmaceutical Production Example 7

Beverages for Muscle Dysfunction Inhibition/Muscular Atrophy Inhibition/Prevention of a Bedridden State (Hereinafter Referred to as "Muscle Dysfunction Inhibition and so on")

Tea-based beverages were prepared from the pharmaceutical product of the present invention according to the formulation and preparation conditions shown in Table 14. The composition of catechin employed for producing the tea-based beverages is shown in Table 15. The thus-prepared beverages exhibited excellent storage stability and good taste.

TABLE 14

Formulation of tea beverages

|  | Green tea beverage | (g/100 mL) Oolong tea beverage |
|---|---|---|
| Green tea extract (g) | 17.5 | 0 |
| Oolong tea extract (g) | 0 | 8 |
| Tea extract (g) | 0.37 | 0.48 |
| Purified water (g) | balance | balance |
| Na ascorbate (g) | 0.05 | 0.05 |
| pH (after sterilization) | 5.98 | 5.87 |
| Sterilization temperature (° C.) | 133 | 134 |
| Heating time for sterilization (sec) | 30 | 30 |
| Container | PET container | PET container |

TABLE 15

Catechin compositions of beverages

|  | Green tea beverage | (mg/500 mL) Oolong tea beverage |
|---|---|---|
| Catechin | 32.4 | 30.7 |
| Epicatechin | 32.7 | 35.6 |
| Gallocatechin | 124.1 | 113.0 |
| Epigallocatechin | 85.8 | 91.8 |
| Catechin gallate | 23.0 | 22.1 |
| Epicatechin gallate | 37.3 | 41.9 |
| Gallocatechin gallate | 94.9 | 86.7 |
| Epigallocatechin gallate | 110.9 | 120.1 |
| Total non-polymer catechins | 541.0 | 541.9 |

Pharmaceutical Production Example 8

Enteral Nutrient for Muscle Dysfunction Inhibition and so on

A pharmaceutical product falling within the scope of the invention having a formulation shown in Table 16 was placed in a retort, followed by sealing. The retort was subjected to high-pressure steam sterilization through a customary method, whereby an enteral nutrient was produced. Minerals employed were in the form of a mixture of organic or inorganic salts of Na, K, Ca, Mg, P, Cl, Fe, etc., and vitamins employed were in the form of a mixture containing vitamins A, D, E, $B_1$, $B_2$, $B_6$, $B_{12}$, C, niacin, pantothenic acid, etc. These minerals and vitamins were employed in amounts according to the Japanese Recommended Dietary Allowance.

TABLE 16

Enteral nutrient formulation

|  | (g/100 mL) |
|---|---|
| Milk casein | 3.40 |
| Separated soybean protein | 1.67 |
| Dextrin | 14.86 |
| Sucrose | 1.30 |
| Soybean oil | 1.75 |
| *Perilla* oil | 0.18 |
| Soybean phospholipid | 0.14 |

TABLE 16-continued

Enteral nutrient formulation

|  | (g/100 mL) |
|---|---|
| Glycerin fatty acid ester | 0.07 |
| Minerals | 0.60 |
| Vitamins | 0.06 |
| Teaflan 90S (product of Ito En Ltd.) | 0.11 |
| Purified water | balance |

Pharmaceutical Production Example 9

Jerry for Muscle Dysfunction Inhibition and so on

A jerry was produced from a pharmaceutical product falling within the scope of the invention. Specifically, a gelling agent mixture of carageenan and locust bean gum (0.65%), grapefruit juice 50% concentrate (5.0%), citric acid (0.05%), vitamin C (0.05%), and Teavigo (product of DSM Nutritional Products) (0.54%) were mixed together, and water was added to the mixture so as to adjust the amount to 100%. The ingredients were dissolved at 65° C. A small amount of grapefruit flavor was added to the solution, and the resultant liquid was maintained at 85° C. for five minutes for sterilization. After sterilization, the liquid was dispensed to 100-mL containers. The dispensed products were allowed to stand for 8 hours to gradually cool to 5° C., thereby forming a catechin-containing jelly. The thus-produced jelly was smoothly melted in the mouth and had favorable fruit flavor and comfortable texture.

Pharmaceutical Production Example 10

Vitamin Oral Liquid for Muscle Dysfunction Inhibition and so on

A vitamin oral liquid was produced from a pharmaceutical product falling within the scope of the invention. Specifically, taurine (800 mg), sucrose (11,000 mg), caramel (50 mg), sodium benzoate (30 mg), vitamin $B_1$ nitrate (5 mg), vitamin $B_2$ (20 mg), vitamin $B_6$ (20 mg), vitamin C (2,000 mg), vitamin E (100 mg), vitamin $D_3$ (2,000 IU), nicotinic acid amide (20 mg), and POLYPHENON 70S (product of Mitsui Norin Co., Ltd.) (540 mg) were added to a suitable amount of purified water, and the pH of the solution was adjusted to 3 by use of aqueous phosphoric acid solution. Purified water was further added to the solution, to thereby adjust the total volume to 50 mL. The mixture was sterilized at 80° C. for 30 minutes, whereby a catechin-containing vitamin oral liquid was produced.

Pharmaceutical Production Example 11

Chewable Tablets for Muscle Dysfunction Inhibition and so on

Chewable tablets were produced from a pharmaceutical product falling within the scope of the invention. Specifically, tablets, having a formulation (daily dose: 1,200 mg) of ascorbic acid (180 mg), citric acid (50 mg), aspartame (12 mg), magnesium stearate (24 mg), crystalline cellulose (120 mg), lactose (274 mg), and Teaflan 90S (product of Ito En Ltd.) (540 mg), were prepared in accordance with the Japanese Pharmacopoeia (General rules for preparations, "Tablets"), whereby catechin-containing chewable tablets were produced.

Pharmaceutical Production Example 12

Tablets for Muscle Dysfunction Inhibition and so on

Catechin-containing tablets were prepared from a pharmaceutical product falling within the scope of the invention through a routine method, which have the following formulation (mass %): POLYPHENON 70S (product of Mitsui Norin Co., Ltd.) (20), sodium malate (20), palatinose (20), ascorbic acid (20), Vitamin Mix (product of The Nippon Koryo Yakuhin Kaisha, Ltd.) (5), crystalline cellulose (5), sucrose ester (4), silicon dioxide (1), and eggshell-derived calcium (5).

Pharmaceutical Production Example 13

Tea-Based Beverages for Muscle Senescence Inhibition

Amino acid-blended tea-based beverages for muscle senescence inhibition falling within a scope of the invention were prepared according to the formulation and preparation conditions shown in Table 17. The thus-prepared beverages exhibited excellent storage stability and good taste.

TABLE 17

Formulation of amino acid-containing tea beverages (g/100 mL)

| | Green tea beverage | Oolong tea beverage |
|---|---|---|
| Green tea extract (g) | 17.5 | 0 |
| Oolong tea extract (g) | 0 | 8 |
| Tea catechin (POLYPHENON 70S) (g) | 0.12 | 0.16 |
| Purified water (g) | balance | balance |
| Na ascorbate (g) | 0.05 | 0.05 |
| Leucine (g) | 0.16 | 0.16 |
| Isoleucine (g) | 0.08 | 0.08 |
| Valine (g) | 0.08 | 0.08 |
| Taurine (g) | 0.05 | 1.00 |
| pH (after sterilization) | 5.98 | 5.87 |
| Sterilization temperature (° C.) | 133 | 134 |
| Heating time for sterilization (sec) | 30 | 30 |
| Container | PET container | PET container |

Pharmaceutical Production Example 14

Non-Tea-Based Beverages for Muscle Senescence Inhibition

Amino acid-blended sport beverages for muscle senescence inhibition falling within a scope of the invention were prepared according to the formulation and preparation conditions shown in Table 18. The thus-prepared beverages exhibited excellent storage stability and good taste.

TABLE 18

| | (g/100 mL) | |
|---|---|---|
| | Formulation 1 | Formulation 2 |
| Catechin (POLYPHENON 70S) (g) | 0.114 | 0.114 |
| Sweetener (aspartame + glucose) (g) | 1.2 | 1.2 |

TABLE 18-continued

| | (g/100 mL) | |
|---|---|---|
| | Formulation 1 | Formulation 2 |
| Acid-flavoring agent (g) | 0.24 | 0.24 |
| Purified water (g) | balance | balance |
| NaCl (g) | 0.04 | 0.04 |
| KCl (g) | 0.009 | 0.009 |
| Flavor (g) | 0.3 | 0.3 |
| Vitamin C (g) | 0.03 | 0.03 |
| Leucine (g) | 0.12 | 0 |
| Isoleucine (g) | 0.06 | 0 |
| Valine (g) | 0.06 | 0 |
| Taurine (g) | 0 | 0.4 |
| pH (after sterilization) | 3.5 | 3.5 |
| Container | PET container | PET container |

Pharmaceutical Production Example 15

Enteral Nutrient for Muscle Senescence Inhibition

Purified water was added to milk casein (3.4 g), separated soybean protein (1.67 g), dextrin (14.86 g), sucrose (1.3 g), soybean oil (1.75 g), perilla oil (0.18 g), soybean phospholipid (0.14 g), glycerin fatty acid ester g), minerals (0.60 g), vitamins (0.06 g), Teaflan 90S (product of Ito En Ltd.) (0.11 g), leucine (0.18 g), isoleucine (0.09 g), and valine (0.09 g). The mixture was placed in a retort pouch and was subjected to high-pressure steam sterilization through a customary method, whereby an enteral nutrient for muscle senescence inhibition (100 mL) containing catechin and amino acids was produced. Minerals employed were in the form of a mixture of organic or inorganic salts of Na, K, Ca, Mg, P, Cl, Fe, etc., and vitamins employed were in the form of a mixture containing vitamins A, D, E, $B_1$, $B_2$, $B_6$, $B_{12}$, C, niacin, pantothenic acid, etc. These minerals and vitamins were employed in amounts according to the Japanese Recommended Dietary Allowance.

Pharmaceutical Production Example 16

Jelly for Muscle Senescence Inhibition

A gelling agent mixture of carageenan and locust bean gum (0.65%), grapefruit juice 50% concentrate (5.0%), citric acid (0.05%), vitamin C (0.05%), Teavigo (product of DSM Nutritional Products) (0.54%), leucine (0.3%), isoleucine (0.15%), valine (0.15%), and taurine (0.5%) were mixed together, and water was added to the mixture so as to adjust the amount to 100%. The ingredients were dissolved at 65° C. A small amount of grapefruit flavor was added to the solution, and the resultant liquid was maintained at 85° C. for five minutes for sterilization. After sterilization, the liquid was dispensed to 100-mL containers. The dispensed products were allowed to stand for 8 hours to gradually cool to 5° C., whereby a jelly for muscle senescence inhibition containing catechin and a branched-chain amino acids was produced. The thus-produced jelly was smoothly melted in the mouth and had favorable fruit flavor and comfortable texture.

Pharmaceutical Production Example 17

Vitamin-Containing Oral Liquid for Muscle Senescence Inhibition

Taurine (800 mg), sucrose (2,000 mg), caramel (50 mg), sodium benzoate (30 mg), vitamin $B_1$ nitrate (5 mg), vitamin $B_2$ (20 mg), vitamin $B_6$ (20 mg), vitamin C (2,000 mg), vitamin E (100 mg), vitamin D₃ (2,000 IU), nicotinic acid amide (20 mg), POLYPHENON 70S (product of Mitsui Norin Co., Ltd.) (50 mg), leucine (200 mg), isoleucine (100 mg), and valine (100 mg) were added to a suitable amount of purified water, and the pH of the solution was adjusted to 3 by use of aqueous phosphoric acid solution. Purified water was further added to the solution, to thereby adjust the total volume to 50 mL. The product was sterilized at 80° C. for 30 minutes, whereby a vitamin oral liquid for muscle senescence inhibition containing catechin and amino acids was produced.

Pharmaceutical Production Example 18

Chewable Tablets for Muscle Senescence Inhibition

Tablets, having a formulation of ascorbic acid (180 mg), citric acid (50 mg), aspartame (12 mg), magnesium stearate (24 mg), crystalline cellulose (120 mg), lactose (274 mg), Teaflan 90S (product of Ito En Ltd.) (300 mg), leucine (600 mg), isoleucine (300 mg), and valine (300 mg), were prepared in accordance with the Japanese Pharmacopoeia (General rules for preparations, "Tablets"), whereby chewable tablets for muscle senescence inhibition containing catechin and amino acids were produced.

Pharmaceutical Production Example 19

Tablets for Muscle Senescence Inhibition

Tablets for muscle senescence inhibition containing catechin and amino acids were prepared through a routine method, which have the following formulation (wt. %): POLYPHENON 70S (product of Mitsui Norin Co., Ltd.) (5), leucine (10), taurine (5), sodium malate (20), palatinose (20), ascorbic acid (20), Vitamin Mix (5), crystalline cellulose (5), sucrose ester (4), silicon dioxide (1), and eggshell-derived calcium (5).

The invention claimed is:

1. A method for inhibiting a condition accompanying senescence, wherein said condition accompanying senescence is muscular atrophy, wherein the method comprises administering a composition comprising (a) 0.1 to 1 wt. % of a catechin and (b) 0.2 to 2 wt. % of a branched amino acid to a subject in need thereof.

2. The method according to claim 1, wherein the branched amino acid is leucine.

3. The method according to claim 1, wherein the composition is a food or beverage.

4. The method according to claim 1, wherein the composition is a food.

5. The method according to claim 1, wherein the composition is a beverage.

* * * * *